(12) United States Patent
Ishikura et al.

(10) Patent No.: US 7,622,450 B2
(45) Date of Patent: Nov. 24, 2009

(54) FLAVONE C-GLYCOSIDE DERIVATIVES AND COMPOSITIONS CONTAINING THE DERIVATIVES

(75) Inventors: Yoshiyuki Ishikura, Osaka (JP); Kuniro Tsuji, Shizuoka (JP); Haruo Nukaya, Shizuoka (JP)

(73) Assignee: Suntory Holdings Limited, Osaka (JP)

( * ) Notice: Subject to any disclaimer, the term of this patent is extended or adjusted under 35 U.S.C. 154(b) by 192 days.

(21) Appl. No.: 10/519,979

(22) PCT Filed: Jul. 3, 2003

(86) PCT No.: PCT/JP03/08481

§ 371 (c)(1),
(2), (4) Date: Aug. 22, 2005

(87) PCT Pub. No.: WO2004/005296

PCT Pub. Date: Jan. 15, 2004

(65) Prior Publication Data

US 2005/0288237 A1 Dec. 29, 2005

(30) Foreign Application Priority Data

Jul. 3, 2002 (JP) .............................. 2002-194828

(51) Int. Cl.
*A01N 43/04* (2006.01)
*A61K 31/70* (2006.01)
*C07H 15/00* (2006.01)
*C07H 17/00* (2006.01)

(52) U.S. Cl. ................................. 514/27; 514/33; 536/8
(58) Field of Classification Search .................... 514/27, 514/33; 536/8
See application file for complete search history.

(56) References Cited

U.S. PATENT DOCUMENTS 5,409,692 A * 4/1995 Nakahara et al. .............. 424/49
2002/0136753 A1 * 9/2002 Uehara et al. ................ 424/442

FOREIGN PATENT DOCUMENTS

| EP | 853943 A1 | 7/1998 |
| JP | 3-157330 A | 7/1991 |
| JP | 10-77231 A | 3/1998 |
| WO | WO 2004/092180 | 10/2004 |

OTHER PUBLICATIONS

Kijoia et al., "Further prenylflavonoids from artocarpus elasticus," Phytochemistry, 1998, pp. 875-878, vol. 47, No. 5, Science Direct—Elsevier B.V., United Kingdom.
Ahluwalia et al., "A new convenient synthesis of benzofluroflavones," Indian Journal of Chemistry, Section B: Organic Chemistry Including Medicinal Chemistry, 1987, pp. 229-231, vol. 26B, No. 3, India.
Jain et al., "Claisen rearrangement of 7-prenyl ethers of chrysin & 3-0-methylgalangin: a novel 3-0-demethylation," Indian Journal of Chemistry, 1973 pp. 723-725, vol. 11, No. 8, India.
Ikegaya, Food Science Series: Tea Science, K. Muramatsu, ed., Asakura Shoten, Tokyo, Japan, pp. 86-94 (1991) (English translation provided).
Japanese Office Action issued Feb. 3, 2009, in Japanese Patent Application No. 2002-194828.
Nakazato et al., "Anti-Inflammatory Effect of Oolong Tea Polyphenols," Nippon Nogeikagaku Kaishi, vol. 72, No. 1, 1998, pp. 53-56 (English-language Abstract).
Shiozaki et al., "Effect of Tea Extracts, Catechin and Caffeine Against Type-Allergic Reaction," Yakagaku Zasshi, vol. 117, No. 7, 1997, pp. 448-454 (English-language Abstract).
Sunaga et al., "Irritation Test of Skin and Eye Mucosa on Oolong Tea Water-Soluble Extracts," Preclin. Rep. Cent. Inst. Exp. Anim., vol. 19, No. 3, 1994, pp. 199-203 (English-language Abstract).
Shiozaki et al., "Antiallergic Effect of Tea," Journal of Traditional Medicines, vol. 11, No. 4, 1994, pp. 444-445 (English-language Abstract).
Maeda-Yamamoto et al., "Effects of Tea Infusions of Various Varieties or Different Manufacturing Types on Inhibition of Mouse Mast Cell Activation," Biosci. Biotechnol. Biochem., vol. 62, No. 11, 1998, pp. 2277-2279.

* cited by examiner

*Primary Examiner*—Traviss C McIntosh, III
(74) *Attorney, Agent, or Firm*—Drinker Biddle & Reath LLP (57) ABSTRACT

The present invention relates to novel flavone C-glycoside derivatives or salts thereof, especially those showing an anti-allergic effect, and compositions containing them. Recently, cases of allergic diseases, especially pollenosis and atopic dermatitis have increased to such a degree that they have become a social problem. Flavones and their glycosides have been reported to have the effect of inhibiting histamine release from mast cells or an immunosuppressive effect and expected for application as allergy therapies. However, most flavones exhibit their effects only at high doses, so that effective compounds at lower doses are highly desired. The present invention provides novel components capable of treating allergic diseases at low doses and compositions containing them.

30 Claims, 2 Drawing Sheets

Fig. 1

(*: p<0.05 vs. control group)

Fig. 2

(*: p<0.05 vs. control group)

Fig. 3

FLAVONE C-GLYCOSIDE DERIVATIVES AND COMPOSITIONS CONTAINING THE DERIVATIVES

TECHNICAL FIELD

The present invention relates to novel flavone C-glycoside derivatives or salts thereof, especially those having anti-allergic effects, and compositions containing them.

BACKGROUND ART

Recently, various epidemiological surveys have shown an increase in allergic diseases. Cases of pollenosis and atopic dermatitis, in particular, are increasing to such a degree that they have become a social problem. Increased allergens and changes in our environment such as air pollution, food additives and changes in dietary habits are thought to cause such an increase in cases of allergic diseases (Itoh, Sōgō rinsyō 41:3099(1992)). Current therapies for allergic diseases basically involve removing or rejecting causal allergens in combination with drug therapy, based on the severity of the symptoms or the pathogenic mechanism of each disease. Allergic reactions are classified into four types, from type I to IV, based on the causal immunoglobulin and immune cells involved. Type I to III allergies, which are called immediate allergies due to the patient's immediate allergic reaction, are immunoreactions in which humoral antibodies are involved, while type IV allergy, which is called delayed allergy, is a cell-mediated immune reaction in which sensitized lymphocytes but not antibodies are involved (Tomioka, Sōgō rinsyō 41:3103 (1992)).

Among these allergic reactions, type I and type IV allergic reactions are thought to be involved in pollenosis and atopic dermatitis, which are treated with antihistamines, basic anti-allergic agents or steroids.

On the other hand, patent applications which relate to antiallergic agents using oolong tea extracts or epigallocatechin gallate in green tea have been filed (JPA HEI 10-077231, JPA HEI 10-175874, Japanese Patent No. 3023962, etc.). Flavones and their glycosides have been reported to have the effect of inhibiting histamine release from mast cells or to have an immunosuppressive effect, and are expected to be used as allergy therapies (Kubo M. et al, Chem. Pharm. Bull. 32: 5051 (1984)). However, most flavones exhibit their effects only at high doses, so that effective compounds at lower doses are highly desired.

DISCLOSURE OF THE INVENTION

An object of the present invention is to isolate/identify compounds having an anti-allergic effect and to provide novel components capable of treating allergic diseases at low doses and compositions containing such components.

In order to solve the problems above, we focused on the anti-allergic effect of oolong tea and closely examined its anti-allergic components, and we found that novel flavone C-glycoside derivatives or salts thereof have the effect of inhibiting ear edema formation induced by 2,4-dinitrofluorobenzene (DNFB) and the effect of inhibiting histamine release from peritoneal mast cells. We also found that they can be applied as active ingredients in pharmaceutical compositions, food compositions or cosmetics. Thus, we achieved the present invention.

BRIEF EXPLANATION OF THE DRAWINGS

FIG. 1 is a graph showing the results of Experimental example 1. Inhibitory effects of compound (1) of the present invention at three concentrations corresponding to oral doses of 0.2, 1.0 and 5.0 μg/kg on mouse ear contact dermatitis as compared with a control group treated with 0.5% sodium carboxymethylcellulose/0.01N hydrochloric acid are shown.

FIG. 2 is a graph showing the results of Experimental example 2. Inhibitory effects of compound (2) of the present invention at three concentrations corresponding to oral doses of 1.0, 10 and 100 μg/kg on mouse ear contact dermatitis as compared with a control group treated with 0.5% sodium carboxymethylcellulose/0.01N hydrochloric acid are shown.

THE MOST PREFERRED EMBODIMENTS OF THE INVENTION

As described above, we focused attention on the anti-allergic effect of oolong tea and closely examined anti-allergic components in oolong tea in order to solve the problems above, and we found that novel flavone C-glycoside derivatives or salts thereof have the effect of inhibiting ear edema formation induced by 2,4-dinitrofluorobenzene (DNFB) and the effect of inhibiting histamine release from peritoneal mast cells. We also found that they can be applied as active ingredients in pharmaceutical compositions, food compositions or cosmetics. Thus, we achieved the present invention.

Accordingly, the present invention relates to a flavone C-glycoside derivative of formula (1):

or a salt thereof.

The present invention also relates to a flavone C-glycoside derivative of formula (2):

or a salt thereof.

The present invention relates to a pharmaceutical composition for preventing and/or treating an allergic disease containing at least one of said flavone C-glycoside derivatives or a salt thereof. It also relates to said pharmaceutical composition wherein said allergic disease is at least one of atopic dermatitis, contact dermatitis or pollenosis.

The present invention relates to a food composition containing at least one of said flavone C-glycoside derivatives (1) or (2) or a salt thereof. The present invention also relates to said food composition in the form of any one of dietary supplements or other nutrient drinks, healthy drinks, healthy teas or other drinks. It also relates to said food composition in the form of any one of confectionery, breads, noodles, processed soy products, dairy products, processed egg products, fish cakes, fats and oils or seasonings.

The present invention also relates to a cosmetic containing at least one of said flavone C-glycoside derivatives (1) or (2) or a salt thereof. The present invention also relates to said cosmetic in the form of any one of skin care products, makeup products, hair cosmetics or bath products.

The flavone C-glycoside derivatives of formula (1) and/or formula (2) or salts thereof according to the present invention can be obtained from tea leaves by e.g. extraction with a solvent under heating, concentration and purification using conventional chemical separation/purification means (e.g. fractionation or chromatography).

Tea leaves that can be used for the preparation include leaves of *Camellia sinensis* and/or processed leaves thereof. Especially preferred is oolong tea. Oolong tea is semi-fermented tea primarily produced in the Fujian or Guangdong Province of mainland China or Taiwan.

The solvent used for elution may be either an aqueous solvent and/or an organic solvent, but preferably an aqueous solvent. The aqueous solvent is desirably water, ethanol or methanol. It may also be water alone or any mixed solution of water and a lower alcohol such as methanol or ethanol.

The ratio of oolong tea leaves to the solvent at extraction process is not specifically limited, either, but preferably, the weight ratio of oolong tea leaves to the solvent is 2-1000, more preferably 5-100 in terms of extraction operation and yield.

The temperature at elution process is not specifically limited so long as it is higher than the melting point of the solvent and lower than its boiling point, but is desirably 10° C. to 100° C. for water or 10° C. to 40° C. for ethanol and methanol. The extraction period preferably ranges from 10 seconds to 24 hours.

Conventional chemical separation/purification means can be used, such as liquid-liquid distribution, thin-layer chromatography, adsorption column chromatography, partition column chromatography, gel filtration column chromatography, ion exchange column chromatography, electrophoresis and high-speed liquid chromatography. If desired, these separation/purification means can be combined to purify the flavone C-glycoside derivatives of formula (1) and formula (2) or salts thereof at high purity.

The flavone C-glycoside derivatives of formula (1) and formula (2) or salts thereof according to the present invention show an anti-allergic effect so that they can be used for various applications such as pharmaceuticals, foods and cosmetics. For pharmaceuticals, the compounds of formula (1) and/or formula (2) or salts thereof can be used as anti-allergic agents, especially for the purpose of treating atopic dermatitis, contact dermatitis and pollenosis because they show the effect of inhibiting DNFB-induced ear edema formation and the effect of inhibiting histamine release. For foods, they can be added as food additives into dietary supplements or health foods for the purpose of alleviating or preventing symptoms of atopic dermatitis, contact dermatitis and pollenosis. They can be added to various foods. For drinks, they can be added into dietary supplements or other nutrient drinks, healthy drinks, healthy teas or other drinks. They can also be added into other foods such as confectionery, breads, noodles, processed soy products, dairy products, processed egg products, fish cakes, fats and oils or seasonings. For cosmetics, the compounds of formula (1) and/or formula (2) or salts thereof can be added into skin care products, foundation or makeup products for the purpose of alleviating or preventing symptoms of atopic dermatitis, contact dermatitis and pollenosis.

As for pharmaceuticals, the compounds of formula (1) and/or formula (2) or salts thereof can be orally administered directly or after dilution in water or the like. Alternatively, they can be formulated with known pharmaceutical carriers. For example, the compounds of formula (1) and/or formula (2) or salts thereof can be administered as oral liquid formulations such as syrups or solid oral formulations such as tablets, capsules, granules and powders containing their extracts or powders in combination with pharmaceutically acceptable carriers. Pharmaceutically acceptable carriers include various conventional pharmaceutical organic or inorganic carrier materials and are added as excipients, lubricants, binders or disintegrants in solid formulations or solvents, excipients, suspending agents or binders in liquid formulations. If desired, pharmaceutical additives such as preservatives, antioxidants, colorants and sweeteners can also be added.

Preferred examples of excipients include lactose, sucrose, D-mannitol, starch, crystalline cellulose and light silicic anhydride. Preferred examples of lubricants include magnesium stearate, calcium stearate, talc and colloidal silica. Preferred examples of binders include combined cellulose, sucrose, D-mannitol, dextrin, hydroxypropylcellulose, hydroxypropylmethylcellulose and polyvinylpyrrolidone. Preferred examples of disintegrants include polyethylene glycol, propylene glycol, D-mannitol, benzyl benzoate, ethanol, tris-aminomethane, cholesterol, triethanolamine, sodium carbonate and sodium citrate. Preferred examples of solvents include purified water, alcohols and propylene glycol. Preferred examples of suspending agents include surfactants such as ethanolamine stearate, sodium lauryl sulfate, lauryl aminopropionic acid, lecithin, benzalkonium chloride, benzethonium chloride and glycerin monostearate; and hydrophilic polymers such as polyvinylalcohol, polyvinylpyrrolidone, sodium carboxymethylcellulose, methylcellulose, hydroxymethylcellulose, hydroxyethylcellulose and hydroxypropylcellulose. Preferred examples of preservatives include paraoxybenzoic acid esters, chlorobutanol, benzyl alcohol, phenethyl alcohol, dehydroacetic acid and sorbic acid. Preferred examples of antioxidants include sulfites and ascorbic acid.

Dosage forms are those suitable for oral, parenteral or nasal administration such as tablets or sugar-coated tablets, sublingual tablets, gelatin capsules, troches, suppositories, creams, ointments and skin gels, depending on the type or severity of the disease. The effective dose depends on the age and body weight of the patient, the type or severity of the disease and the route of administrate. The unit dose is generally in the range of 0.0001 to 100 mg/kg, which is administered one to three times in 24 hours.

As for foods, the compounds of formula (1) and/or formula (2) or salts thereof can be administered as such or in the form of foods or drinks containing their extracts or powders. They can also be provided as drinks, confectionery, breads, noodles, processed soy products, dairy products, processed egg products, fish cakes, fats and oils or seasonings in combination with conventional materials for foods and drinks and carriers acceptable for ingredients of foods and drinks.

As used herein, drinks includes oolong tea drinks, tea drinks mixed with other tea drinks, carbonated drinks, fruit drinks, lactic acid bacterial beverage, isotonic drinks, soy milk and liquors such as wine, distilled spirit, whisky and sake mixed with oolong tea drinks or other tea drinks.

As used herein, confectionery includes biscuits, chocolates, candies, chewing gums, snacks, fried cakes, Western fresh cakes, Japanese traditional cakes, ice creams and jellies.

Processed soy products include bean curd, and dairy products include yogurt and butter. Processed egg products include omelet and pot-steamed hotchpotch, and fish cakes include fish sausage. Seasonings include sauces, dressings, mayonnaise and various fish and vegetables flakes. These can be prepared by conventional processes.

Carriers acceptable for ingredients of foods and drinks include sweeteners such as sugar, glucose, fructose, isomerized liquid sugar, fructooligosaccharides, aspartame, sorbitol and stevia; colorants such as red cabbage dye, grape skin dye, elderberry dye, caramel, gardenia dye, corn dye, saffron dye and carotene; preservatives such as pectin hydrolysate, benzoic acid, sorbic acid, paraoxybenzoic acid esters and potassium sorbate; gelling agents such as sodium alginate, propylene glycol alginate ester, calcium cellulose glycolate and sodium cellulose glycolate; antioxidants such as L-ascorbic acid, tocopherol, erythorbic acid and rutin; color fixing agents such as ferrous sulfate, sodium nitrite and potassium nitrate; bleaching agents such as sodium bisulfite and potassium metabisulfite; quality-keeping agents such as propylene glycol; quality improvers such as L-cysteine hydrochloride and calcium stearyl lactate; leavening agents such as ammonium chloride, potassium hydrogen d-tartrate, ammonium carbonate, potassium carbonate, sodium bicarbonate and alum; emulsifiers such as lecithin, sphingolipids, vegetable sterol, soybean saponin, sodium alginate, propylene glycol alginate ester, sodium caseinate, glycerin fatty acid ester, sucrose fatty acid ester and sorbitan fatty acid ester; emulsion stabilizer such as sodium chondroitin sulfate; flavors such as lemon oil, eucalyptus oil, peppermint oil, vanilla extract, orange oil, garlic oil, ethyl acetoacetate, anisaldehyde, ethyl vanillin, cinnamic acid, citronellyl acetate, citral, vanillin, butyl butyrate and esters; health builders such as L-ascorbic acid, L-asparagine, L-alanine, inositol, L-glutamine, carotene, tocopherol, vitamin A, folic acid, iron citrate, heme iron and uncalcined calcium; flour improvers such as benzoyl peroxide, ammonium persulfate and chlorine dioxide; bactericides such as bleaching powder, hydrogen peroxide and hypochlorous acid; chewing gum bases such as methyl acetyl ricinoleate, ester gum, vinyl acetate resin, polyisobutylene and polybutene; anti-caking agents such as D-mannitol; binders such as acidic sodium pyrophosphate, potassium pyrophosphate and sodium pyrophosphate; acidifiers such as adipic acid, citric acid, gluconic acid, succinic acid, d-tartaric acid, lactic acid and dl-malic acid; and seasonings such as seafood extracts, yeast extracts, seaweed extracts, soybean sauce, tomato puree, meat extracts, Japanese sweet rice wine for cooking, fruit purees, boiled and dried bonito flesh, sodium L-aspartate, DL-alanine, L-arginine, L-glutamates, disodium 5'-inosinate, trisodium citrate, L-glutamic acid, sodium L-glutamate, succinic acid, L-tartaric acid and sodium lactate.

The compounds of formula (1) and/or formula (2) or salts thereof according to the present invention can be provided directly or after dilution in water or the like or after concentration or disintegration or granulation in combination with known carriers, in the form of aerosols, solutions, extracts, suspensions, emulsions, ointments, poultices, liniments and lotions. Alternatively, they are prepared by appropriately selecting aqueous components, surfactants, oily components, solubilizers, humectants, powder components, alcohols, pH modifiers, preservatives, antioxidants, thickeners, dyes, pigments and perfumes used in known cosmetics, quasi drugs and drugs. They can also be provided in dosage forms for topical skin application such as lotions, gels, emulsions and ointments.

As used herein, skin care products include skin lotions such as emollient lotion and astringent lotion; creams such as emollient cream, moisturizing cream and massage cream; and emulsions such as emollient emulsion, nourishing emulsion and cleansing emulsion.

Makeup cosmetics include face washes, skin cleansers, foundations, eye colors, cheek colors and lip colors.

Hair cosmetics include shampoos, rinses, hair treatment agents, hair creams, hairdressings, hair tonics, hair growing agents and hair growth promoters. Bath products include bath oils, bath salts and bath foams.

The concentration in foods and cosmetics is not specifically limited either, but preferably 0.0001-100% by weight, especially 0.001-50% by weight expressed as dry solids.

The following experimental examples and working examples further illustrate the present invention without, however, limiting the scope of the present invention exclusively thereto.

EXAMPLES

Example 1

Preparation Example

Oolong tea leaves in an amount of 5.0 kg produced in the Fujian Province of mainland China were extracted with 100 L of hot water, and the extracts were allowed to cool and then applied on a column packed with 30 L of a synthetic adsorbent (DIAION HP-21, Mitsubishi Chemical). Unadsorbed fractions were applied on a column packed with 30 L of a synthetic adsorbent (DIAION HP-20, Mitsubishi Chemical) and eluted with serially increasing concentrations of ethanol in water (each 60 L) to give 4 fractions [ethanol concentrations=0% (OHF3N), 20% (OHF4N), 40% (OHF5N), 99.5% (OHF6N)].

Among these 4 fractions, OHF3N fraction showed the strongest inhibitory effect on DNFB-induced ear edema. The formation was concentrated and freeze-dried (517 g) and subjected to countercurrent distribution in a water-n-butanol system (n=7) and the fraction after 7 transfers was concentrated under reduced pressure (2.1 g). Then the resultant was applied on a column packed with Sephadex LH-20 (Pharmacia Biotech) and eluted with methanol, and fractions in the range of 1.9-2.2 Kd were collected. The fractions were concentrated under reduced pressure and separated by HPLC on a column SENSHU PAK DIOL-1251 (SENSHU Scientific, 4.6×250 mm) using a solvent hexane:methanol:tetrahydrofuran=50:35:15 as a mobile phase at a flow rate of 1 ml/min (30° C.), and a peak (detected by UV 280 nm) eluted at a retention time of 5.8 minutes was collected. After concentration under reduced pressure, the fraction was purified by HPLC using YMC-Pack ODS-A (YMC, 4.6×150 mm). The purified product was collected and then concentrated under reduced pressure to give 980 µg of a pale yellow powder.

Figure 3:
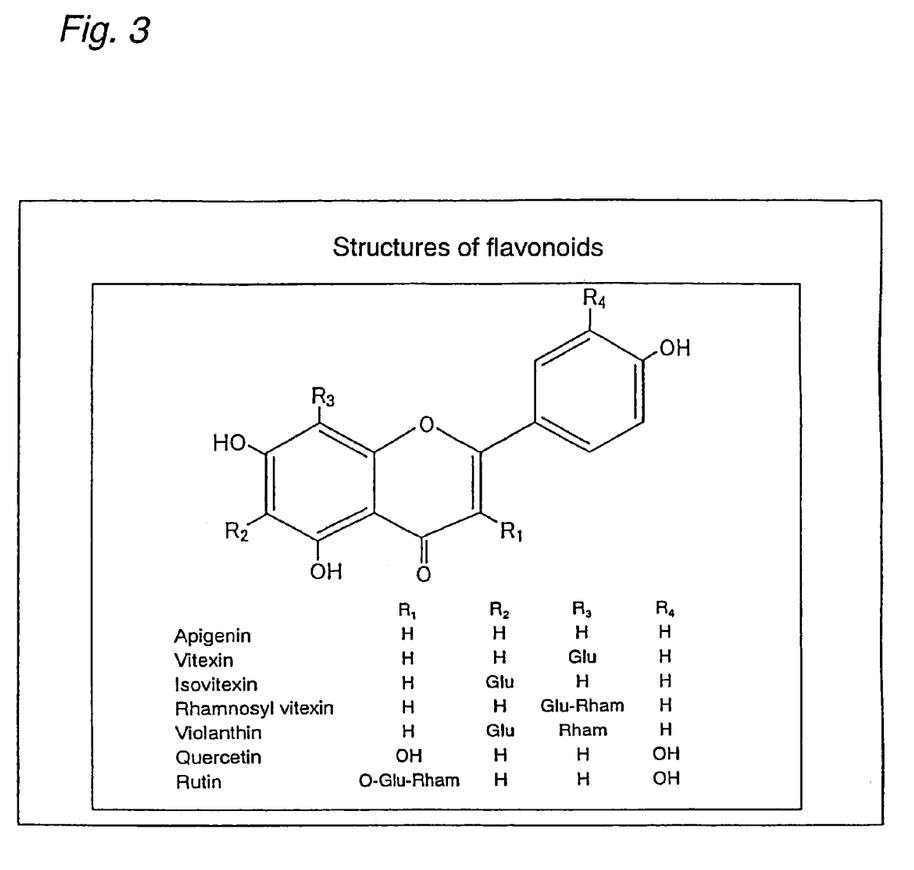
FIG. 3 shows the structures of flavonoids.

As a result of structural analysis by spectrometric techniques such as NMR and MS and X-ray analysis (see Table 1 and Table 2), the present compound was identified as a compound of formula (1) [compound (1)] produced by intramolecular dehydration condensation between the 7-OH of Isovitexin (see FIG. 3) and the 1-OH on the sugar chain.

TABLE 1

Structural determination of compound (1) by $^1$H-NMR and $^{13}$C-NMR

| moiety | Aglycone C | Aglycone H | | Sugar C | Sugar H |
|---|---|---|---|---|---|
| 2 | 168.1 | | 1" | 74.6 | 5.21 d |
| 3 | 102.9 | 6.58 s | 2" | 89.0 | 4.67 t |
| 4 | 184.8 | | 3" | 73.9 | 3.98 t |
| 5 | 168.7 | | 4" | 69.8 | 3.58 t |
| 6 | 112.6 | | 5" | 80.6 | 3.33 m |
| 7 | 166.5 | | 6" | 63.5 | 3.62 m, 3.83 m |
| 8 | 91.8 | 6.64 s | | | |
| 9 | 161.2 | | | | |
| 10 | 107.9 | | | | |
| 1' | 119.3 | | | | |
| 2' | 130.2 | 7.80 d | | | |
| 3' | 119.3 | 6.80 d | | | |
| 4' | 168.1 | | | | |
| 5' | 119.3 | 6.80 d | | | |
| 6' | 130.2 | 7.80 d | | | |

Structural determination of compound (1) by $^1$H-NMR and $^{13}$C-NMR (ppm. in $CD_3OD$)

TABLE 2

Structural determination of compound (1) by X-ray analysis

| Crystal Dimensions | 0.10 × 0.05 × 0.20 mm |
|---|---|
| Lattice Parameters | a = 10.811(6) Å |
| | b = 26.270(6) Å |
| | c = 6.905(1) Å |
| | V = 1961.0(9) Å$^3$ |
| Space Group | P2$_1$2$_1$2$_1$ |
| Z value | 4 |
| D$_{calc}$ | 1.403 g/cm$^3$ |
| R value | 0.078 |

During the purification process of compound (1), OHF3N fraction (517 g) was subjected to countercurrent distribution in a water-n-butanol system (n=7) and the fraction after 7 transfers was concentrated under reduced pressure (2.1 g). Then, the resultant was applied on a column packed with Sephadex LH-20 (Pharmacia Biotech) and eluted with methanol, and fractions in the range of 1.6-1.9 Kd were collected. The fractions were concentrated under reduced pressure and separated by HPLC on a column SENSHU PAK DIOL-1251 (SENSHU Scientific, 4.6×250 mm) using a solvent hexane:methanol:tetrahydrofuran=50:35:15 as a mobile phase at a flow rate of 1 ml/min (30° C.) and a peak (detected by UV 280 nm) eluted at a retention time of 5.8 minutes was collected. After concentration under reduced pressure, the fraction was purified by HPLC using YMC-Pack ODS-A (YMC, 4.6×150 mm). The purified product was collected and then concentrated under reduced pressure to give 147 μg of a pale yellow powder.

As a result of structural analysis by spectrometric techniques such as NMR and MS and X-ray analysis (see Table 3 and Table 4), the present compound was identified as a compound of formula (2) [compound (2)] produced by intramolecular dehydration condensation between the 7-OH of Vitexin (see FIG. 3) and the 1-OH on the sugar chain.

TABLE 3

Structural determination of compound (2) by $^1$H-NMR and $^{13}$C-NMR

| moiety | Aglycone C | Aglycone H | | Sugar C | Sugar H |
|---|---|---|---|---|---|
| 2 | 166.8 | | 1" | 75.1 | 5.47 d |
| 3 | 104.3 | 6.66 s | 2" | 89.1 | 4.78 t |
| 4 | 184.4 | | 3" | 73.8 | 4.05 t |
| 5 | 166.2 | | 4" | 69.8 | 3.62 t |
| 6 | 96.3 | 6.39 s | 5" | 80.5 | 3.47 m |
| 7 | 168.9 | | 6" | 63.4 | 3.65 m, 3.87 m |
| 8 | 108.5 | | | | |
| 9 | 155.1 | | | | |
| 10 | 106.7 | | | | |
| 1' | 125.0 | | | | |
| 2' | 130.2 | 7.90 d | | | |
| 3' | 118.0 | 6.93 d | | | |
| 4' | 164.9 | | | | |
| 5' | 118.0 | 6.93 d | | | |
| 6' | 130.2 | 7.90 d | | | |

Structural determination of compound (2) by $^1$H-NMR and $^{13}$C-NMR (ppm. in $CD_3OD$)

TABLE 4

Structural determination of compound (2) by X-ray analysis

| Crystal Dimensions | 0.03 × 0.10 × 0.30 mm |
|---|---|
| Lattice Parameters | a = 9.785(2) Å |
| | b = 19.700(5) Å |
| | c = 4.9357(8) Å |
| | V = 950.1(3) Å$^3$ |
| Space Group | P2$_1$ |
| Z value | 2 |
| D$_{calc}$ | 1.560 g/cm$^3$ |
| R value | 0.058 |

Experimental Example 1

Inhibitory Effect on Mouse Ear Contact Dermatitis

Figure 1:
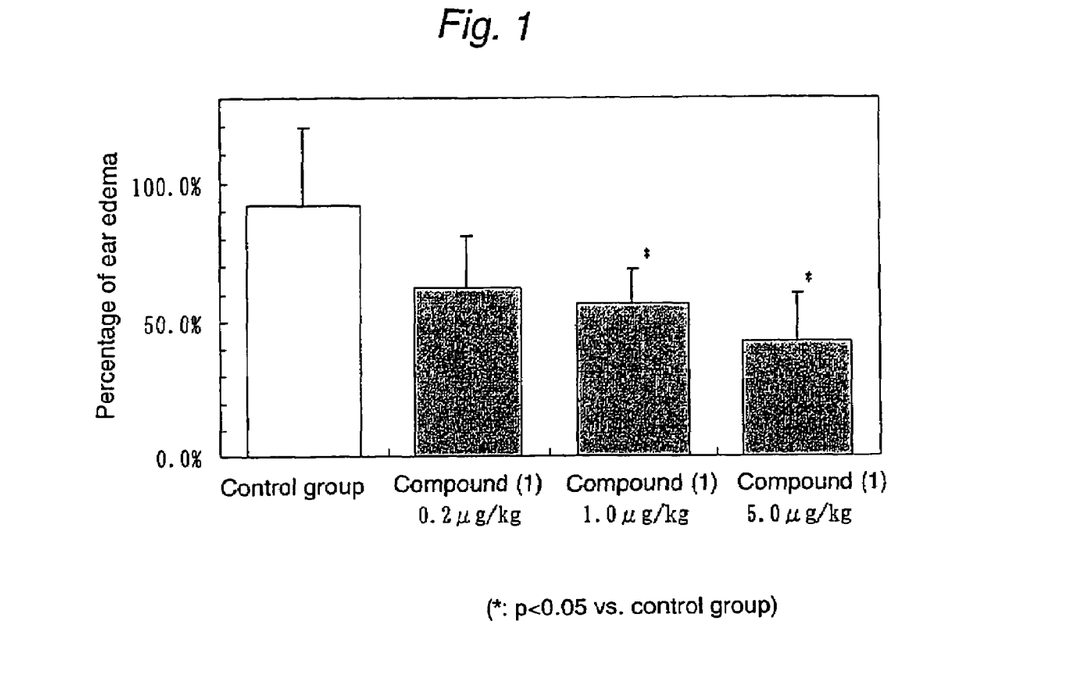

ICR strain mice at 7 weeks of age were purchased from CLEA Japan and used for experiments after preconditioning for 1 week. The yellow powder obtained in Example 1 [compound (1)] was suspended in 0.5% sodium carboxymethylcellulose/0.01N hydrochloric acid to prepare sample formulations at three concentrations corresponding to doses of 0.2, 1.0 and 5.0 μg/kg in a dose volume of 10 ml/kg. Infection in six mice per group was established in 5 days by subcutaneous injection of 100 μl of a solution of 1% 2,4-dinitrofluorobenzene (DNFB) in ethanol on the back. On day 6, a solution of 1% DNFB in olive oil was applied on the right ear to induce ear contact dermatitis. After 24 hours, both ears were punched out in a diameter of 8 mm and weighed. Compound (1) was continuously orally administered for 7 days from the day before the primary challenge until the day on which edema was induced. A control group was treated with 0.5% sodium carboxymethylcellulose/0.01N hydrochloric acid. The experimental results were expressed as the average percentage of edema on the right in relation to left ears with standard deviation using Student's t-test for evaluating the significance between groups. The results are shown in FIG. 1. As shown in FIG. 1, DNFB-induced edema was significantly inhibited in the groups treated with 1.0 and 5.0 μg/kg of compound (1) as compared with the control group treated with 0.5% sodium carboxymethylcellulose/0.01N hydrochloric acid.

Experimental Example 2

Inhibitory Effect on Mouse Ear Contact Dermatitis

Figure 2:
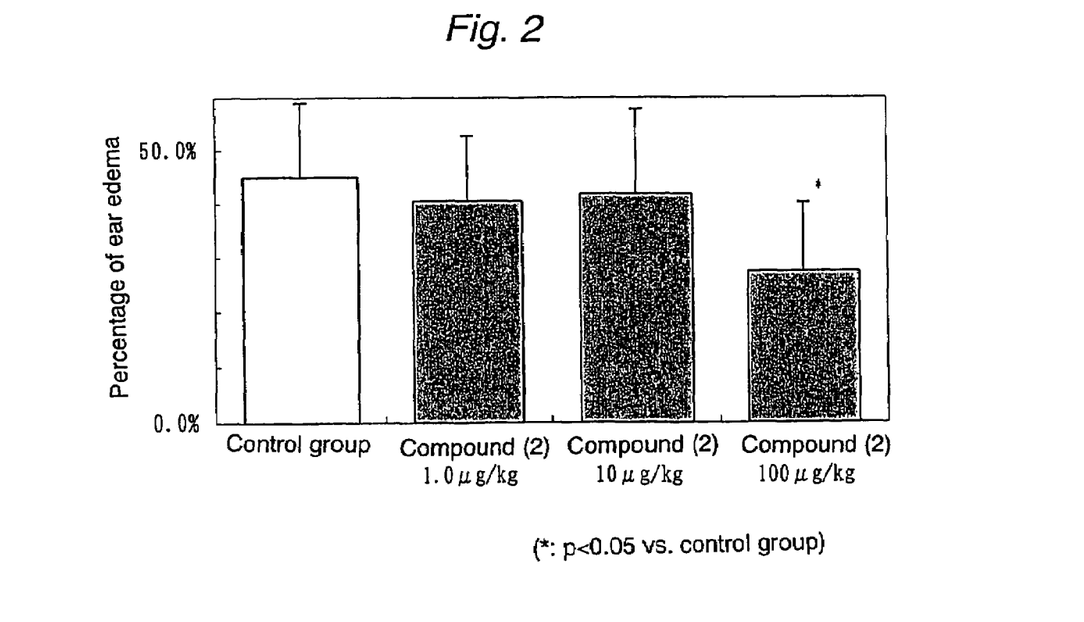

ICR strain mice at 7 weeks of age were purchased from CLEA Japan and used for experiments after preconditioning for 1 week. The yellow powder obtained in Example 1 [compound (2)] was suspended in 0.5% sodium carboxymethylcellulose/0.01N hydrochloric acid to prepare sample formulations at three concentrations corresponding to doses of 1.0, 10 and 100 µg/kg in a dose volume of 10 ml/kg. Infection in six mice per group was established in 5 days by subcutaneous injection of 100 µl of a solution of 1% 2,4-dinitrofluorobenzene (DNFB) in ethanol on the back. On day 6, a solution of 1% DNFB in olive oil was applied on the right ear to induce ear contact dermatitis. After 24 hours, both ears were punched out in a diameter of 8 mm and weighed. Compound (2) was continuously orally administered for 7 days from the day before the primary challenge until the day on which edema was induced. A control group was treated with 0.5% sodium carboxymethylcellulose/0.01N hydrochloric acid. The experimental results were expressed as the average percentage of edema on the right in relation to left ears with standard deviation using Student's t-test for evaluating the significance between groups. The results are shown in FIG. 2. As shown in FIG. 2, DNFB-induced edema was significantly inhibited in the group treated with 100 µg/kg of compound (2) as compared with the control group treated with 0.5% sodium carboxymethylcellulose/0.01N hydrochloric acid.

Experimental Example 3

Inhibitory Effect on Histamine Release from Peritoneal Mast Cells

Wistar strain rats at 7 weeks of age were purchased from CLEA Japan and used for experiments after preconditioning for 1 week. After Wistar strain rats were decapitated under ether anesthesia, Tyrode solution was intraperitoneally injected. Mast cells were routinely isolated and suspended at $1-3\times10^8$ cells/ml in Tyrode solution containing 0.1% bovine serum albumin (BSA) to prepare a mast cell suspension. The mast cell suspension was incubated with compound (1) or compound (2) dissolved in 50% methanol at 37° C. for 5 minutes. Then, the suspension was further incubated with Compound 48/80 at 37° C. for 10 minutes and cooled on ice and then centrifuged. Then, the free histamine content in the resulting supernatant was measured on a high-speed liquid chromatograph by the post-column method using ortho-phthalaldehyde (OPA) according to the method of Onda et al. [J. Med. Sci., 27, 93-97(1978)]. The experimental results were expressed as the percentage of histamine release inhibited by the treatment with the samples as compared with the treatment with the solvent alone. The results are shown in Table 5.

TABLE 5

Results of histamine release inhibition test

| Sample | Concentration (µg/ml) | Histamine release inhibition (%) |
|---|---|---|
| Compound (1) | 5.0 | 62.3 |
| Compound (2) | 50.0 | 51.2 |

Example 2

Comparison with the Effects of a Steroid and Other Flavonoids

The same procedures as in Experimental examples 1 and 2 were used to compare the inhibitory effects of a corticosteroid and several flavonoids (FIG. 3) on DNFB-induced ear edema formation with those of compound (1) and compound (2). The experimental results were expressed as the dose producing a 50% inhibition of DNFB-induced ear edema. The results are shown in Table 6.

Administration of compound (1) and compound (2) showed an inhibitory effect on ear edema formation at very smaller doses than the corticosteroid or other flavonoids.

TABLE 6

Evaluation results of inhibitory effect on ear edema formation

| | Dose producing 50% inhibition of ear edema (mg/kg p.o.) |
|---|---|
| Compound (1) | 0.05 |
| Compound (2) | 0.17 |
| Dexamethasone | 1.5 |
| Apigenin | 247 |
| Vitexin | 103 |
| Rhamnosyl vitexin | 146 |
| Quercetin | 265 |
| Rutin | 123 |

Example 3

Preparation Example of Tablets

Tablets each having a diameter of 10 mm and a weight of 300 mg were prepared by mixing 150 g of compound (1) obtained in Example 1 with the same amount of lactose and 5 g of magnesium stearate and compressing this mixture using a single stroke tablet press.

Example 4

Preparation Example of Granules

The tablets obtained in Example 3 were ground, granulated and sieved to give granules of 20-50 meshes.

Example 5

Preparation Example of Hard Candies

The following materials were used to prepare hard candies according to a conventional process.

| | |
|---|---|
| Sorbitol powder | 99.7 g |
| Perfume | 0.2 g |
| Compound (1) | 0.05 g |
| Sorbitol seed | 0.05 g |
| Total | 100 g |

Example 6

Preparation Example of Chewing Gum

The following materials were used to prepare chewing gum according to a conventional process.

| | |
|---|---|
| Gum base | 20 g |
| Calcium carbonate | 2 g |
| Stevioside | 0.1 g |
| Compound (1) | 0.05 g |
| Lactose | 76.85 g |
| Perfume | 1 g |
| Total | 100 g |

Example 7

Preparation Example of Tangerine Juice

The following materials were used to prepare tangerine juice according to a conventional process.

| | |
|---|---|
| Frozen concentrated tangerine juice | 5 g |
| Fructose-glucose syrup | 10 g |
| Citric acid | 0.2 g |
| L-ascorbic acid | 0.02 g |
| Compound (1) | 0.05 g |
| Perfume | 0.2 g |
| Dye | 0.1 g |
| Water | balance |
| Total | 100 g |

Example 8

Preparation Example of Jelly Candies

The following materials were used to prepare jelly candies.

| | |
|---|---|
| Sugar | 500 g |
| Starch syrup | 500 g |
| Pectin | 13 g |
| Citric acid | 4 g |
| Sodium citrate | 1.5 g |
| Perfume | 1 g |
| Food color | 0.2 g |
| Compound (1) | 0.5 g |

A mixture of 13 g of pectin and 20 g of sugar was homogeneously dissolved in 330 ml of water. The mixed solution was combined with citric acid and sodium citrate and boiled. The mixed solution was combined with starch syrup and heated to 100° C., and then combined with the remainder of sugar and heated to 109° C. After standing for several minutes, the mixture was stirred with compound (1), perfume and dye and charged into starch molds and dried at 50° C. or less for 10 hours or more to give jelly candies.

Example 9

Preparation Example of Fish Sausage

The following materials were used to prepare fish sausage.

| | |
|---|---|
| Minced cod flesh | 100 g |
| Salt | 20 g |
| Condiment | 2 g |
| Egg white | 10 g |
| Compound (1) | 0.5 g |

Minced cod flesh was kneaded with salt, condiment and compound (1) and aged. Then the paste was shaped and steamed in a steamer preheated at about 90-95° C., and then allowed to cool to give fish sausage.

Example 10

Preparation Example of Emollient Cream

The following materials were used to prepare emollient cream according to a conventional process.

| | |
|---|---|
| Beeswax | 2.0 g |
| Stearyl alcohol | 5.0 g |
| Stearic acid | 8.0 g |
| Squalane | 10.0 g |
| Self-emulsifying propylene glycol monostearate | 3.0 g |
| Polyoxyethylene cetyl ether | 1.0 g |
| Perfume | 0.5 g |
| Preservative | q.l. |
| Antioxidant | q.l. |
| Propylene glycol | 7.8 g |
| Glycerin | 4.0 g |
| Sodium hyaluronate | 0.15 g |
| Compound (1) | 0.05 g |
| Triethanolamine | 1.0 g |
| Purified water | 57.5 g |

Example 11

Preparation Example of Shampoo

The following materials were used to prepare shampoo according to a conventional process.

| | |
|---|---|
| Sodium alkyl ether sulfate | 16.0 g |
| Diethanolamide laurate | 4.0 g |
| Propylene glycol | 1.95 g |
| Preservative, dye, perfume | q.l. |
| Antioxidant | q.l. |
| Compound (1) | 0.05 g |
| Purified water | 78.0 g |

INDUSTRIAL APPLICABILITY

According to the present invention, it was found that novel flavone C-glycoside derivatives contained in oolong tea leaves or salts thereof have a remarkable anti-allergic effect and pharmaceutical compositions, food compositions or cosmetics containing them as active ingredients can be provided, as described above.

The invention claimed is:

1. An isolated flavone C-glycoside derivative of formula (1):

or a salt thereof.

2. An isolated flavone C-glycoside derivative of formula (2):

or a salt thereof.

3. A method for the preparation of a pharmaceutical composition, food composition, or cosmetic having an anti-allergic effect, comprising adding at least one of the flavone C-glycoside derivative according to claim 1 or salt thereof to said pharmaceutical composition, food composition, or cosmetic.

4. A method for the preparation of a pharmaceutical composition, food composition or cosmetic having an anti-allergic effect, comprising adding at least one of the flavone C-glycoside derivative according to claim 2 or salt thereof to said pharmaceutical composition, food composition or cosmetic.

5. A pharmaceutical composition containing at least about 0.001 weight % dry solids of one of the flavone C-glycoside derivative or salt thereof according to claim 1 to treat an allergic disease.

6. The pharmaceutical composition according to claim 5 wherein said allergic disease is at least one selected from atopic dermatitis, contact dermatitis and pollenosis.

7. A food composition containing at least about 0.001 weight % dry solids of one of the flavone C-glycoside derivative or salt thereof according to claim 1 as an anti-allergic component to treat an allergic disease.

8. The food composition according to claim 7 in the form of any one of dietary supplements or other nutrient drinks, healthy drinks, healthy teas or other drinks.

9. The food composition according to claim 7 in the form of any one of confectionery, breads, noodles, processed soy products, dairy products, processed egg products, fish cakes, fats and oils or seasonings.

10. A cosmetic containing at least about 0.001 weight % dry solids of one of the flavone C-glycoside derivative or salt thereof according to claim 1 as an anti-allergic component to treat an allergic disease.

11. The cosmetic according to claim 10 in the form of any one of skin care products, makeup products, hair cosmetics or bath products.

12. A method for the preparation of a pharmaceutical composition, food composition, or cosmetic having an anti-allergic effect, comprising adding at least about 0.001 weight % dry solids of one of the flavone C-glycoside derivative according to claim 1 or salt thereof to said pharmaceutical composition, food composition, or cosmetic.

13. A method for the preparation of a pharmaceutical composition, food composition or cosmetic having an anti-allergic effect, comprising adding at least about 0.001 weight % dry solids of one of the flavone C-glycoside derivative according to claim 2 or salt thereof to said pharmaceutical composition, food composition or cosmetic.

14. A pharmaceutical composition containing at least about 0.001 weight % dry solids of one of the flavone C-glycoside derivative or salt thereof according to claim 2 to treat an allergic disease.

15. The pharmaceutical composition according to claim 14, wherein said allergic disease is at least one selected from atopic dermatitis, contact dermatitis and pollenosis.

16. A food composition containing at least about 0.001 weight % dry solids of one of the flavone C-glycoside derivative or salt thereof according to claim 2 as an anti-allergic component to treat an allergic disease.

17. The food composition according to claim 16 in the form of any one of dietary supplements or other nutrient drinks, healthy drinks, healthy teas or other drinks.

18. The food composition according to claim 16 in the form of any one of confectionery, breads, noodles, processed soy products, dairy products, processed egg products, fish cakes, fats and oils or seasonings.

19. A cosmetic containing at least about 0.001 weight % dry solids of one of the flavone C-glycoside derivative or salt thereof according to claim 2 as an anti-allergic component to treat an allergic disease.

20. The cosmetic according to claim 19 in the form of any one of skin care products, makeup products, hair cosmetics or bath products.

21. A flavone C-glycoside derivative of formula (1) purified to at least about 0.001 weight % dry solids:

or a salt thereof.

22. A flavone C-glycoside derivative of formula (2) purified to at least about 0.001 weight % dry solids:

or a salt thereof.

23. A method of treating an allergic disease, comprising: administering to a patient in need of treatment for an allergic disease a therapeutically effective amount of at least one of the flavone C-glycoside derivative or salt thereof according to claim 1.

24. A method of treating an allergic disease, comprising: administering to a patient in need of treatment for an allergic disease a therapeutically effective amount of at least one of the flavone C-glycoside derivative or salt thereof according to claim 2.

25. A method of treating an allergic disease, comprising: administering to a patient in need of treatment for an allergic disease the pharmaceutical composition according to claim 5.

26. A method of treating an allergic disease, comprising: administering to a patient in need of treatment for an allergic disease the food composition according to claim 7.

27. A method of treating an allergic disease, comprising: administering to a patient in need of treatment for an allergic disease the cosmetic according to claim 10.

28. A method of treating an allergic disease, comprising: administering to a patient in need of treatment for an allergic disease the pharmaceutical composition according to claim 14.

29. A method of treating an allergic disease, comprising: administering to a patient in need of treatment for an allergic disease the food composition according to claim 16.

30. A method of treating an allergic disease, comprising: administering to a patient in need of treatment for an allergic disease the cosmetic according to claim 19.

* * * * *